(12) United States Patent
Pittaway et al.

(10) Patent No.: US 9,387,303 B2
(45) Date of Patent: Jul. 12, 2016

(54) SYSTEM FOR THE MANAGEMENT OF MEDICAL TUBING

(75) Inventors: Alan Pittaway, High Wycombe (GB); William Barnes, Reading (GB)

(73) Assignee: Intersurgical AG, Vaduz (LI)

( * ) Notice: Subject to any disclaimer, the term of this patent is extended or adjusted under 35 U.S.C. 154(b) by 0 days.

(21) Appl. No.: 12/782,795

(22) Filed: May 19, 2010

(65) Prior Publication Data

US 2010/0294271 A1 Nov. 25, 2010

(30) Foreign Application Priority Data

May 20, 2009 (GB) .................................. 0908691.9

(51) Int. Cl.
*F16L 3/22* (2006.01)
*A61M 16/08* (2006.01)
*A61M 5/14* (2006.01)
*F16L 3/13* (2006.01)

(52) U.S. Cl.
CPC .......... *A61M 16/0875* (2013.01); *A61M 5/1418* (2013.01); *F16L 3/13* (2013.01); *F16L 3/22* (2013.01); *A61M 2209/082* (2013.01)

(58) Field of Classification Search
CPC ..... F16L 3/237; F16L 3/32235; F16L 3/1091; F16L 3/13; F16L 3/22; F21V 21/088; F21V 21/08; F16M 11/041; F16M 11/04; E04C 5/167; E04C 5/163; A61M 16/0875; A61M 5/1418; A61M 2209/082
USPC ................ 248/65, 68.1, 70, 72, 74.2, 231.61, 248/74.1, 73, 316.1, 916, 222.11, 224.8, 248/225.11, 225.21, 74.4, 229, 229.16, 248/229.13, 229.14, 229.15, 229.1, 223.41, 248/223.31, 231.11; 24/664, 665, 669, 672, 24/596.1, 598.1, 593.1, 594.1, 573.11, 24/578.12, 578.14, 580.1, 580.11
See application file for complete search history.

(56) References Cited

U.S. PATENT DOCUMENTS

| | | | | |
|---|---|---|---|---|
| 1,032,436 A | * | 7/1912 | Smith | 24/11 CT |
| 2,657,442 A | * | 11/1953 | Bedford, Jr. | 248/74.2 |
| 2,897,992 A | * | 8/1959 | Nungester | 215/293 |
| 3,561,630 A | * | 2/1971 | Smedstad | 215/308 |
| 4,419,794 A | * | 12/1983 | Horton et al. | 24/667 |
| 4,639,980 A | | 2/1987 | Peterson | |
| 4,688,961 A | * | 8/1987 | Shioda et al. | 403/389 |
| 4,707,906 A | | 11/1987 | Posey | |
| 5,020,749 A | * | 6/1991 | Kraus | 248/74.3 |
| 5,054,170 A | * | 10/1991 | Otrusina | 24/580.11 |
| 5,201,858 A | * | 4/1993 | Otrusina | 24/573.11 |

(Continued)

FOREIGN PATENT DOCUMENTS

| | | | | |
|---|---|---|---|---|
| EP | 0 337 606 A1 | 10/1989 | | |
| GB | 2391543 A | * | 2/2004 | B65D 51/24 |

(Continued)

OTHER PUBLICATIONS

European Search Report for European Patent Application No. 10 163 312.1 (Feb. 25, 2015).

*Primary Examiner* — Kimberly Wood
(74) *Attorney, Agent, or Firm* — LeClairRyan, a Professional Corporation (57) ABSTRACT

A system for the management of medical tubing, the system includes a tube holder adapted for receiving and retaining medical tubes, and a clip adapted to be engaged with a substrate, in which the tube holder may be releasably engaged with the clip.

14 Claims, 8 Drawing Sheets

(56) References Cited

U.S. PATENT DOCUMENTS

| | | |
|---|---|---|
| 5,336,179 A | 8/1994 | Ryan |
| 5,507,460 A | 4/1996 | Schneider |
| 5,542,159 A * | 8/1996 | Schultz et al. .................. 24/341 |
| 5,620,120 A * | 4/1997 | Tien ................................ 224/199 |
| 5,677,513 A * | 10/1997 | Ito et al. ...................... 174/72 A |
| 5,709,665 A | 1/1998 | Vergano et al. |
| 5,833,100 A * | 11/1998 | Kim ............................... 224/197 |
| 5,906,031 A * | 5/1999 | Jensen ............................ 24/3.12 |
| 5,944,696 A | 8/1999 | Bayless et al. |
| 6,061,880 A | 5/2000 | Senninger |
| 6,269,573 B1 * | 8/2001 | Najmi ............................. 40/666 |
| 6,315,250 B1 * | 11/2001 | Meyer .......................... 248/74.1 |
| 6,361,523 B1 | 3/2002 | Bierman |
| 6,375,017 B1 | 4/2002 | Schattner et al. |
| 6,641,093 B2 * | 11/2003 | Coudrais ......................... 248/73 |
| 6,695,269 B1 * | 2/2004 | Anscher ................. 248/225.11 |
| 6,786,372 B2 * | 9/2004 | Enkerlin et al. ............... 224/271 |
| 6,792,653 B2 * | 9/2004 | Protz ................................ 24/485 |
| 7,464,908 B2 * | 12/2008 | Files ........................ 248/229.16 |
| 8,011,071 B2 * | 9/2011 | O'Brien ...................... 24/573.11 |
| 2003/0047575 A1 | 3/2003 | Enkerlin |
| 2003/0188403 A1 | 10/2003 | Lemke et al. |
| 2005/0113718 A1 * | 5/2005 | Butler et al. .................. 600/573 |
| 2005/0258204 A1 * | 11/2005 | Evans et al. ................... 224/197 |
| 2006/0253103 A1 * | 11/2006 | Utterberg et al. ............. 604/533 |
| 2008/0121763 A1 | 5/2008 | Mori et al. |
| 2008/0237282 A1 * | 10/2008 | Sin ................................ 224/197 |
| 2009/0019678 A1 | 1/2009 | Taylor |
| 2009/0094799 A1 | 4/2009 | Ashel |

FOREIGN PATENT DOCUMENTS

| | | |
|---|---|---|
| WO | 2005/051472 A2 | 6/2005 |
| WO | 2005/112555 A2 | 12/2005 |

* cited by examiner

SYSTEM FOR THE MANAGEMENT OF MEDICAL TUBING

This application claims the benefit of United Kingdom Patent Application Ser. No. 0908691.9, filed May 20, 2009, which is hereby incorporated by reference in its entirety.

FIELD

This invention relates to improvements in the management of medical tubing, and in particular to apparatus for improving the organization of tubes that connect a patient to one or more items of medical equipment.

BACKGROUND

In clinical environments, a patient may be connected to one or more items of medical equipment by a number of tubes of various kinds. For instance, breathing circuits, pressure or data lines may connect the patient to equipment such as ventilators or anaesthesia machines. As a result, a multitude of tubes of varying lengths and diameters may be draped over the bed or operating table on which the patient lies, as well as over equipment in the vicinity of the bed or operating table and over the patient himself.

Not least for reasons of patient safety, it is considered good practice for such a multiplicity of tubes to be organized into tidy and manageable groups, and many attempts have been made in the past to facilitate management of medical tubes in this way. Many different designs of clip have been proposed, the effects of which have been to couple together bundles of tubes into a group. Other designs have included the facility to fix the clip to an external support, such as a metal clamp.

Hitherto, no entirely satisfactory system for the management of medical tubes has been provided, and it is an object of this invention to provide a system that improves upon previously-disclosed attempts to address this need.

SUMMARY

According to a first aspect of the invention, there is a provided a system for the management of medical tubing, the system including a tube holder adapted to receive and retain at least one medical tube, and a clip adapted to be engaged with a substrate; wherein the tube holder and the clip are provided with cooperating formations such that the tube holder may be releasably engaged with the clip.

The tube holder may itself constitute a clip with resilient limbs that define a tube-receiving space. Such a holding clip may be engaged with a tube at a point intermediate the ends of the tube. Most preferably, the tube holder has the form of a holding clip with resilient limbs that define a plurality of tube-receiving spaces, and so is adapted to couple together a plurality of medical tubes. The tube holder may be configured such that the tube-receiving spaces are of dimensions appropriate to types of differing medical tubes that are commonly used together, e.g., the tube holder may be adapted to couple together a plurality of tubes having various standard diameters.

Alternatively, the tube holder may have the form of a closure adapted to be engaged with the open end of a tube that is not in use, thereby closing the open end of the tube and preventing ingress of dust or the like during the period in which the tube is not being used.

The substrate with which the clip may be engaged may be any suitable surface or item conventionally found in the vicinity of a patient in a clinical setting. In certain embodiments, the clip may have a pair of resiliently biased jaws that may be caused to part to enable the clip to be attached to a substrate such as bed linen on the patient's bed, or to the patient's clothing or to surgical drapes, or to the frame of the patient's bed or to other suitably shaped hardware in the vicinity. In other embodiments, the clip may be configured such that it can be engaged with a rail of the type that is commonly present on medical equipment used at a patient's bedside or in an operating theatre, such as a ventilator or an anaesthesia machine. Other forms of fastening may also be used, e.g., adhesive pads or hook-and-loop fasteners.

The cooperating formations of the clip and the tube holder most conveniently take the form of a projection, i.e., a lug or stud, on one of those components that is releasably received within a recess or opening in the other. Most commonly, the projection is formed on the tube holder. The projection advantageously has an enlarged head and the recess or opening is configured in such a way as to retain that enlarged head.

The projection may be releasably received within the corresponding recess or opening with a push-fit engagement. For example, the projection may be retained within the corresponding recess or opening by the action of gravity. Alternatively, the projection may be retained within the corresponding recess or opening by a latch or the like.

Typically, the system according to the first aspect of the invention is for the management of respiratory tubing.

Thus, in another aspect of the invention, a holder for a medical tube includes a pair of limbs that define a tube-receiving space into which the medical tube may be inserted, wherein the holder is provided with a projection that may be engaged with a clip that is, or may be, fastened to a substrate.

Typically, the holder further includes a pair of resilient limbs for receiving one or more wires, and most preferably a plurality of wires, therebetween. These wires may be wires that lead to sensors or the like. In presently preferred embodiments, where the holder has two or more tube-receiving spaces, the wire-receiving space defined by these resilient limbs is located between adjacent tube receiving spaces defined by the holder. Each of the resilient limbs may include a plurality of recesses which define depressions for receiving the wires. The ends of the limbs may be bent outwardly to define an entrance for the wires.

According to a further aspect of the invention, there is provided a clip for use with a system according to the first aspect of the invention, wherein the clip is adapted to be engaged with a substrate, and the clip includes a recess or opening adapted to releasably receive a projection of the tube holder. Typically, the tube holder has an enlarged head and the recess or opening of the clip is configured in such a way as to retain that enlarged head.

For many applications, the clip incorporates a retainer for preventing disengagement of the tube holder from the clip. Such a retainer may take the form of a latch or the like that prevents inadvertent disengagement, but which can be released in order to permit disengagement.

In a particular embodiment of the clip according to the invention, the clip includes a pair of jaw members that are biased by a spring to an operative condition in which the jaw members grip a substrate located, in use, between them, and at least one of said jaw members includes a recess adapted to receive and retain a projection provided on a holder for a medical tube, and a latch mechanism retains the projection within the recess, wherein the spring and the latch mechanism are integrally formed such that the spring may be resiliently deformed in a first plane, and the latch mechanism may be resiliently deformed in a second plane that is substantially transverse to the first plane. Such embodiments permit, in a particularly convenient manner, independent opening of the jaw members to permit engagement of the clip with a substrate and release of the latch mechanism to permit disengagement of the tube holder from the clip.

Most conveniently, the components of the present invention are manufactured in plastics material, most commonly by injection moulding.

BRIEF DESCRIPTION OF THE DRAWINGS

Embodiments of the invention will now be described in greater detail, by way of illustration only, with reference to the accompanying drawings, in which.

DETAILED DESCRIPTION

Referring first to FIGS. 1 to 4, a first embodiment of a clip according to the invention is generally designated 10. The clip includes first and second jaws 11, 12 that are formed as a single component by injection moulding and are pivotally connected by an integral hinge 13 in a central region thereof. The jaws 11, 12 are biased to a closed, operative condition (as shown in the drawings) by a resilient leaf spring 14. The jaws 11, 12 are dimensioned and configured such that they can be squeezed together, against the action of the spring 13, between the thumb and forefinger of a user's hand. The outwardly directed surfaces of the jaws 11,12 are provided with ridged finger grips 15, 16 to facilitate such action. By squeezing the jaws 11, 12 together, the distal ends of the jaws 11, 12 are moved apart, enabling the clip 10 to be engaged with, for instance, the patient's bed linen (e.g., a pillow, blanket or sheet) or to a surgical drape or the patient's clothing or any other convenient substrate. Release of the jaws 11, 12 causes the clip 10 to return to the closed, operative condition, the bed linen or other substrate being held securely between the distal ends of the jaws 11, 12, such that the clip 10 is anchored to that substrate. To further enhance the secure attachment of the clip 10 to the substrate, the juxtaposed distal ends of the jaws 11, 12 are provided with teeth 17, 18 that engage with the substrate.

Figure 4:
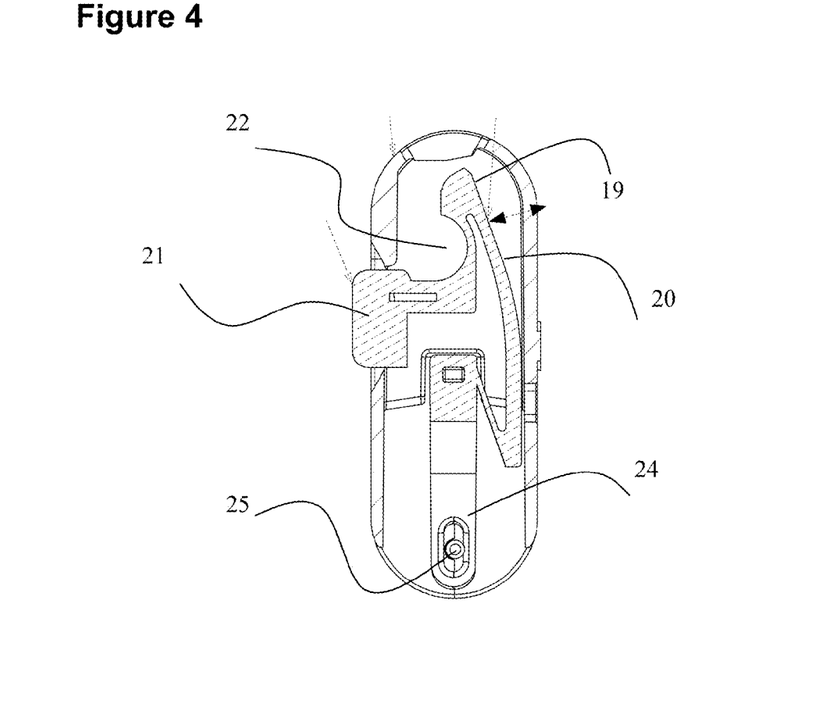
FIG. 4 is a sectional view on the line IV-IV in FIG. 3.

The leaf spring 14 is formed integrally with a latching mechanism that is accommodated within a hollow interior of the first jaw 11 and is shown most clearly in FIG. 4. The latching mechanism includes a detent 19 that is biased by a resilient limb 20 into the position shown in FIG. 4. An extension of the detent 19 constitutes an actuator 21, that protrudes through an opening in the side of the first jaw 11. By depression of the actuator 21, the detent 19 can be displaced from the position shown in FIG. 4, against the action of the resilient limb 20. The detent 19 is formed with an arcuate recess that constitutes a lug receiving space 22. The underside of the detent 19 is undercut such that the recess denoted 22 in FIG. 4 is of greater dimension than the arcuate recess in the upper surface of the detent 19 (which is visible in FIG. 2).

Figure 1:
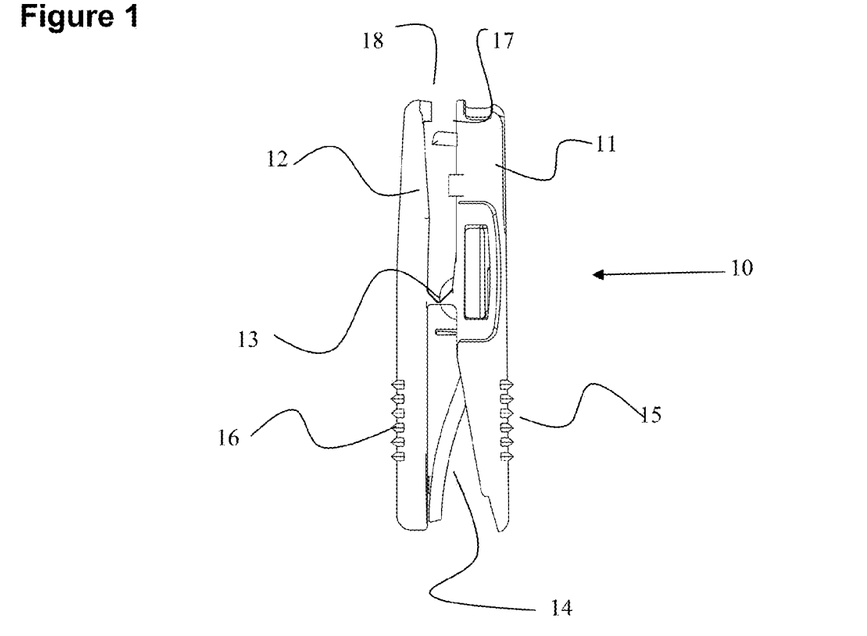
FIG. 1 is a side view of a first embodiment of a clip according to the invention.
Figure 2:
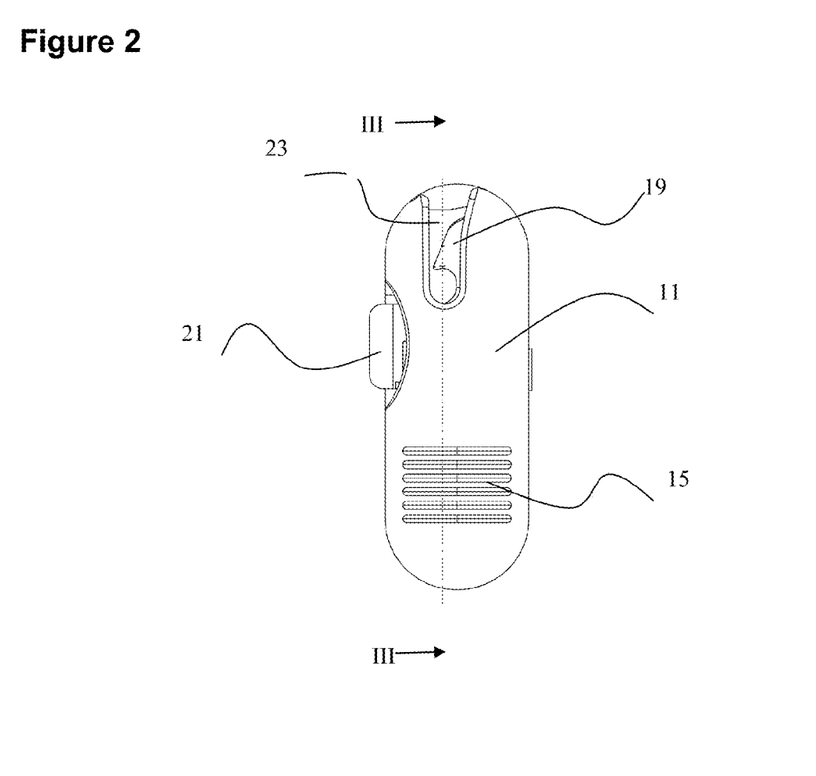
FIG. 2 is a plan view of the clip of FIG. 1.
Figure 3:
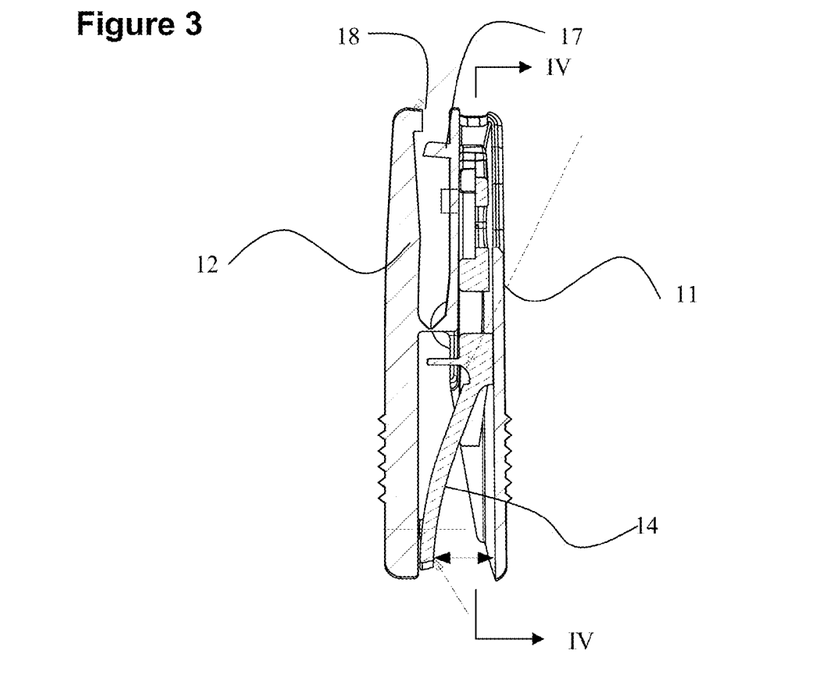
FIG. 3 is a sectional view on the line III-III in FIG. 2.

The first limb 11 is formed with a slot 23 that terminates in registration with the lug receiving space 22. As can be seen in FIG. 2, the detent 19 is visible in the space beneath the slot 23, but can be displaced from the slot 23 by depression of the actuator 21. The edge of the detent 19 is angled relative to the slot 23 so that when a tube holder is engaged with the clip 10 by insertion of a lug into the slot 23, as described below, the lug bears against the detent 19 with a camming action, so that the detent 19 is displaced against the action of the resilient limb 20.

The clip 10 includes just two components: the hingedly connected first and second jaws 11, 12 and the leaf spring 13/latching mechanism assembly. The clip 10 is assembled by snap-fitting the latter assembly into the hollow interior of the first limb 11. The end of the leaf spring 14 is formed with a slot 24 that engages a small peg 25 on the internal surface of the first jaw 11, to anchor the leaf spring 14 in place.

Figure 9:
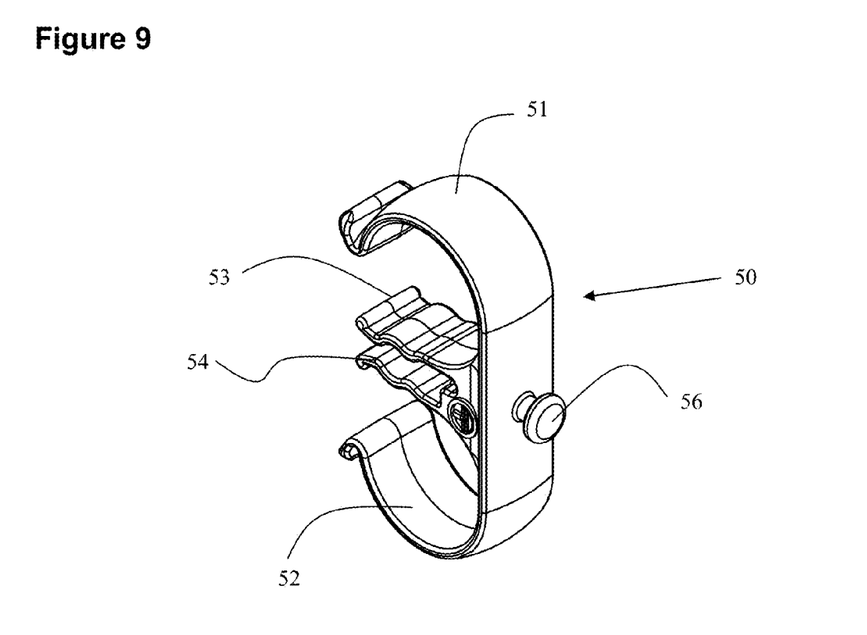
FIG. 9 is a perspective view of a second embodiment of a tube holder according to the invention.
Figure 10:
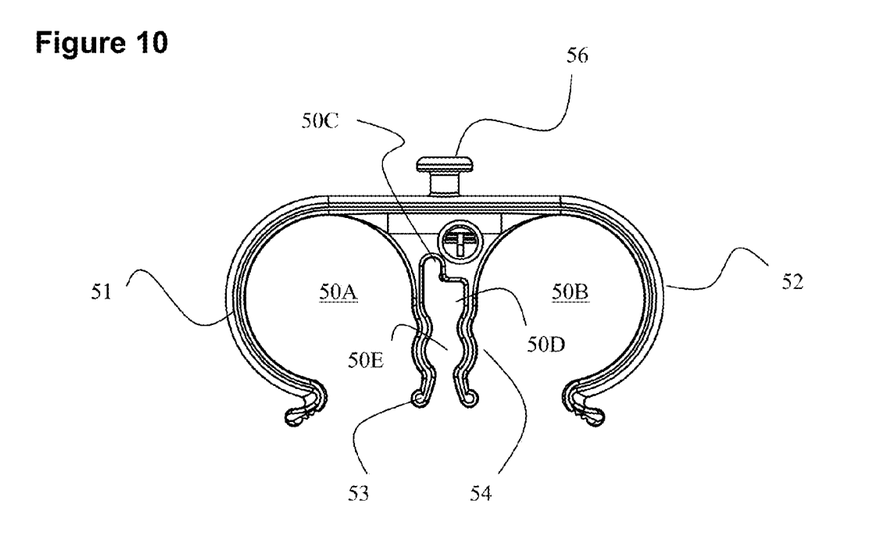
FIG. 10 is a side view of the tube holder of FIG. 9.
Figure 11:
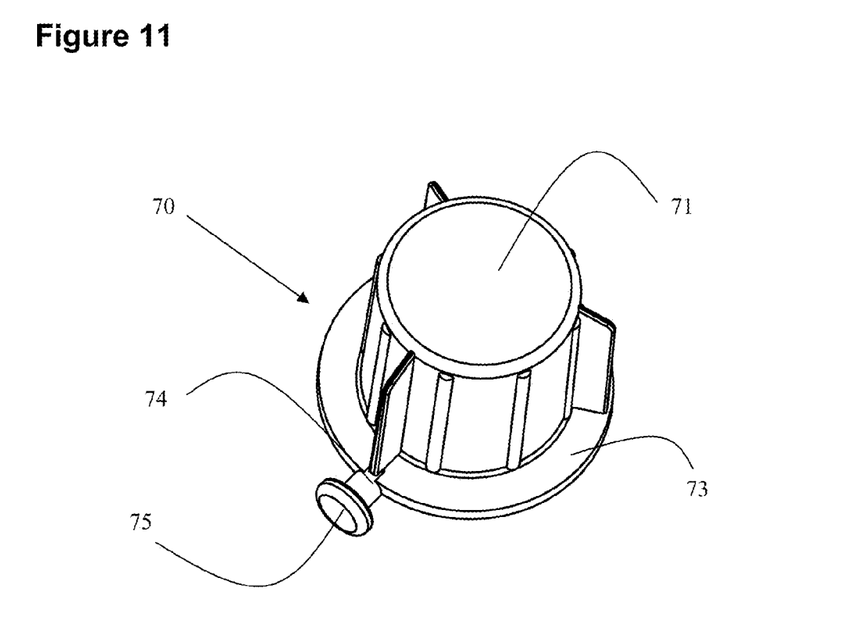
FIG. 11 is a perspective view of a tube cap according to the invention.
Figure 12:
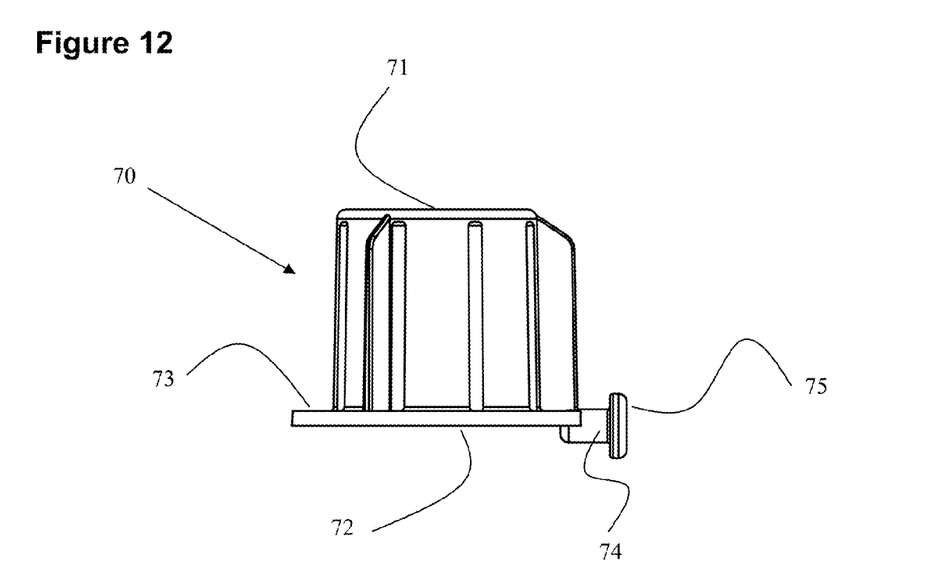
FIG. 12 is a side view of the tube cap of FIG. 11.

The clip 10 is used in association with tube holders of the type illustrated in FIGS. 7 to 10 and/or the tube cap of FIGS. 11 and 12.

Figure 7:
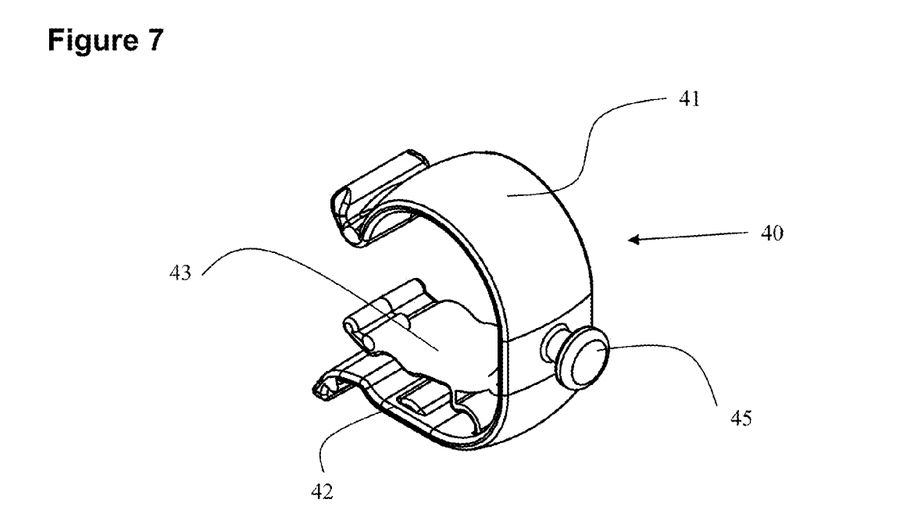
FIG. 7 is a perspective view of a first embodiment of a tube holder according to the invention.
Figure 8:
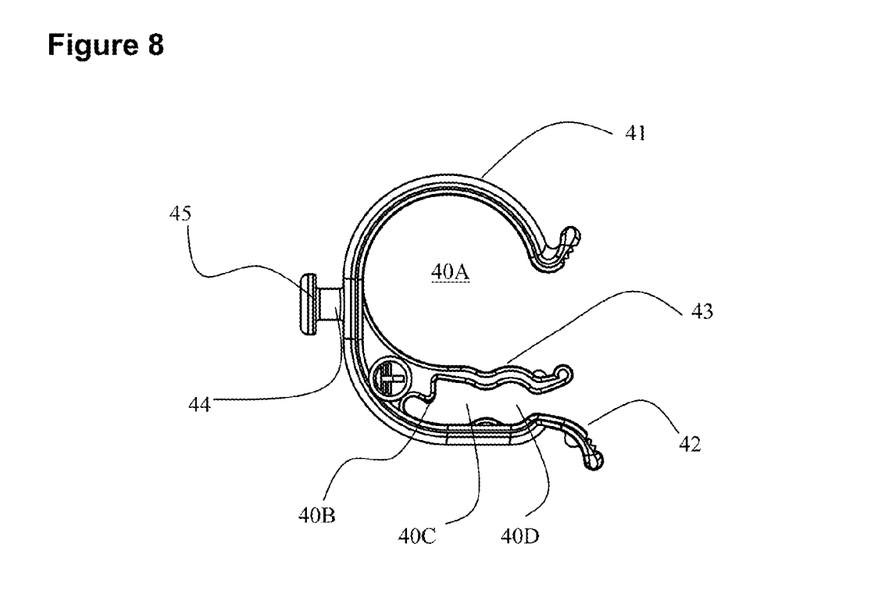
FIG. 8 is a side view of the tube holder of FIG. 7.

Referring to FIGS. 7 and 8, a first embodiment of a tube holder is generally designated 40. The tube holder 40 is formed by injection moulding in plastics material and includes outer resilient limbs 41, 42 that are together arranged generally in a C-shape. A third, intermediate limb 43 is disposed between the outer limbs 41, 42 and divides the space between those outer limbs 41, 42 into several tube receiving spaces. A first tube receiving space 40A is defined between the limbs 41 and 43. The space 40A is dimensioned such that a first, relatively large diameter (e.g. 22 mm) tube can be closely received within it. The juxtaposed surfaces of the limbs 42 and 43 are countoured in such a way that three further tube receiving spaces 40B, 40C and 40D are defined. These spaces are dimensioned to receive relatively small diameter tubes.

The rear face of the clip 40 is formed with a stud-like projection or lug 44 with an enlarged head 45.

In use, the tube holder 40 is engaged with the clip 10 by insertion of the lug 44 into the slot 23. The lug 44 bears against the edge of the detent 19. When the lug 44 is pressed into the slot 23, the detent 19 is displaced, allowing the lug 44 to travel fully into the slot 23. When the lug 44 clears the end of the detent 19, the detent 19 returns to the position shown in FIG. 2, where it acts as a latch, captivating the lug 44 within the slot 23. The enlarged head 45 of the lug 44 is held within the enlarged space 22 in the underside of the detent 19.

Figure 13:
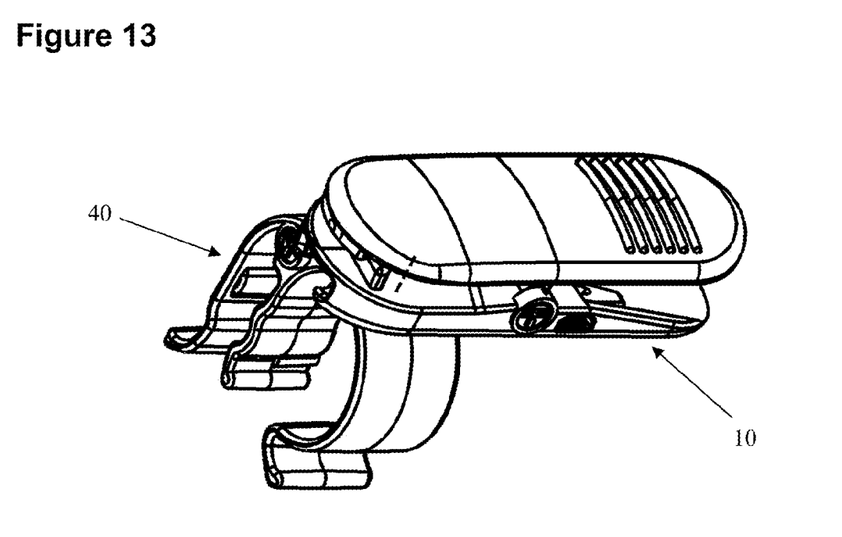
FIG. 13 is a perspective view of the tube holder of FIG. 7 engaged with the clip of FIG. 1.

FIG. 13 shows a tube holder 40 engaged with a clip 10 in this manner.

In order to bundle medical tubes together, and secure them to, for instance, a patient's bed, the following operations are carried out:

a) the tubes are inserted into the tube-receiving spaces in the tube holder 40;

b) the tube holder 40 is engaged with the clip 10; and c) the clip 10 is fastened to the bed linen.

These operations may be carried out in any order. For instance, the tubes may be inserted into the tube holder 40 and/or the clip 10 attached to the bed linen, before the tube holder 40 is engaged with the clip 10, or the tube holder 40 may be connected to the clip 10 before the tubes are inserted into the tube holder 40 and/or the clip 10 is engaged with the bed linen.

To release the tube holder 40 from the clip 10, the actuator 21 is depressed, thereby displacing the detent 19 and allowing the lug 44 to be drawn out of the slot 23.

FIGS. 9 and 10 show a second form of tube holder, generally designated 50. This embodiment is similar in concept to that of FIGS. 7 and 8, save that its outer limbs 51, 52 are configured to define two receiving spaces 50A and 50B, for relatively large diameter tubes. Two intermediate limbs 53, 54 are provided, and are contoured such that three further tube-receiving spaces 50C, 50D, 50E are defined between them, for relatively small diameter tubes. The tube holder 50 can thus accommodate up to five tubes. Like the embodiment of FIGS. 7 and 8, the tube holder 50 is formed with a lug 55 having an enlarged head 56. The tube holder 50 can be coupled to the clip 10 in exactly the same manner as the tube holder 40 of FIGS. 7 and 8.

Figure 15:
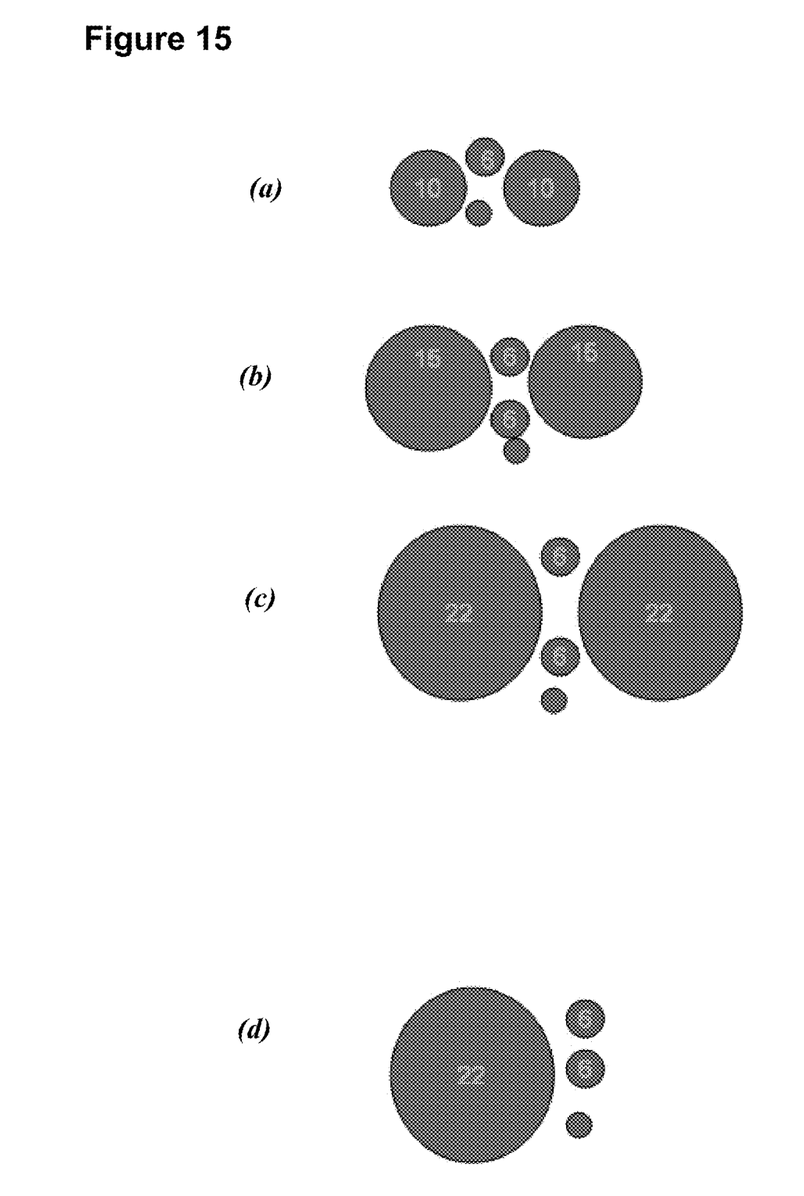
FIG. 15 shows schematically a number of different ways in which tubes may be organized using tube holders of the form illustrated in FIGS. 7 and 9.

FIG. 15 shows schematically the manner in which bundles of medical tubes of various diameters may be held within tube holders of the form depicted in FIGS. 9 and 10 (FIG. 15(*a*)-(*c*)) or the form depicted in FIGS. 7 and 8 (FIG. 15(*d*)), as follows:

FIG. 15(*a*): arrangement of two tubes with an approximate 10 mm diameter and two smaller tubes in a tube holder of the form shown in FIGS. 9 and 10, and having a first (smallest) size;

FIG. 15(*b*): arrangement of five tubes, two with and approximate 15 mm diameter and three smaller tubes in a tube holder of the form shown in FIGS. 9 and 10, and having a second (intermediate) size;

FIG. 15(*c*): arrangement of five tubes, two with an approximate 22 mm diameter and three smaller tubes in a tube holder of the form shown in FIGS. 9 and 10, and having a third (largest) size; and FIG. 15(*d*): arrangement of four tubes, one with an approximate 22 mm diameter and three smaller tubes in a tube holder of the form shown in FIGS. 7 and 8.

Figure 5:
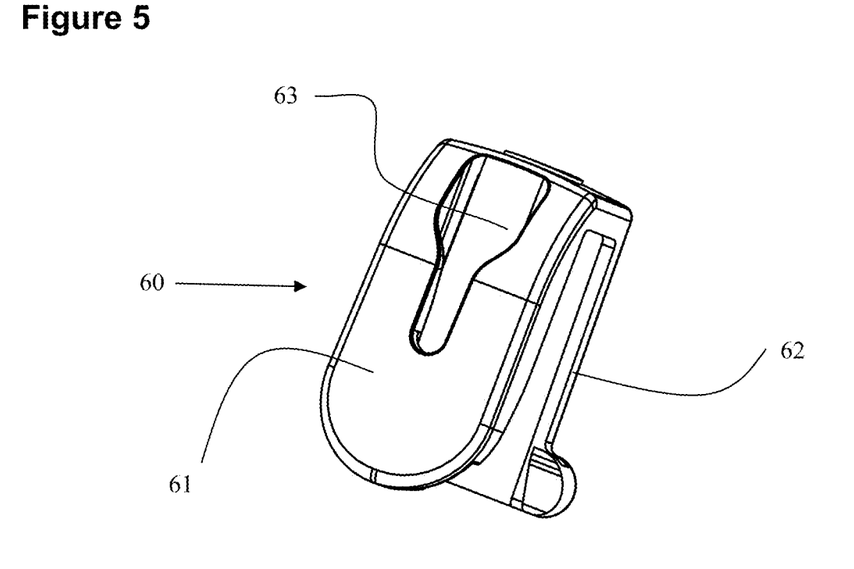
FIG. 5 is a perspective view of a second embodiment of a clip according to the invention.
Figure 6:
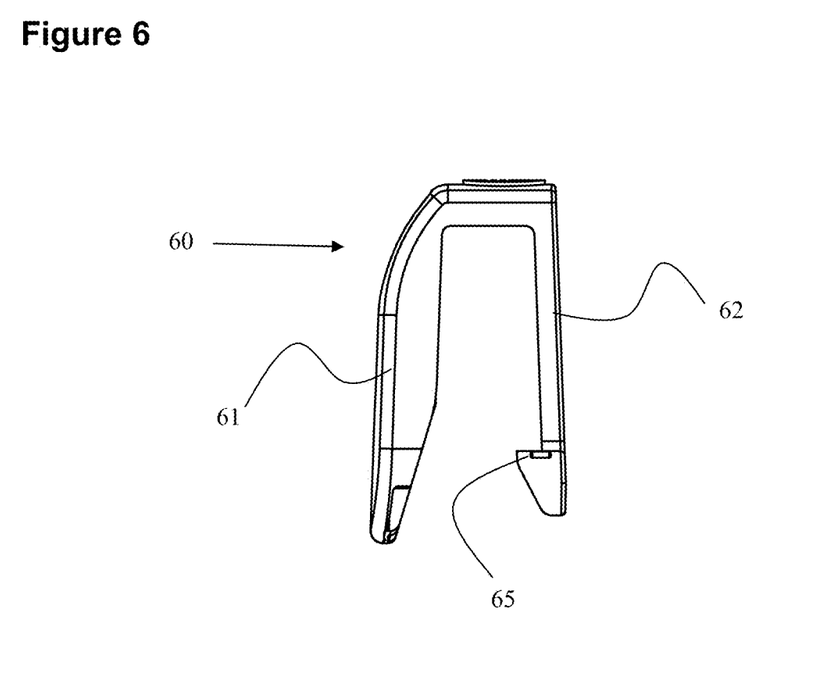
FIG. 6 is a side view of the clip of FIG. 5.

Referring now to FIGS. 5 and 6, a second form of clip according to the invention is designated 60. The clip 60 includes front and rear downwardly depending limbs 61, 62, with a space between them that permits the clip 60 to be hooked over a rail (not shown), as commonly forms part of medical equipment, e.g., a ventilator or anaesthesia machine, disposed alongside a patient's bed of an operating table. The rear limb 62 is formed with an inwardly projecting lip 65 to facilitate retention of the clip 60 on such a rail. The clip 60 may alternatively be fastened to a substrate by an adhesive pad (not shown) applied to the back of the rear limb 62.

The front limb 61 of the clip 60 has a greater depth than the rear limb 61, and is hollow. The front surface of the clip 60, including an inclined upper face of the front surface, is formed with a slot 63 having an enlarged upper part that is able to receive the enlarged head 45, 56 of the lug 44, 55 of a tube holder 40, 50. The lower part of the slot 63 is narrower, such that the enlarged head 45, 56 is retained behind it. Thus, a tube holder 40, 50 can be coupled to the clip 60 simply by inserting the lug 44, 55 into the slot 63. Since the clip 60 incorporates no means for positive retention of the tube holder 40, 50, but instead relies on gravity, the clip 60 can generally only be used in an upright orientation, unlike the clip 10 of FIGS. 1 to 4. An exception to this would be where the head 45, 56 of the lug 44, 55 is received within the slot 63 with an interference fit. In another alternative, the lug 45,56 could have a snap fit with the slot 63.

Figure 14:
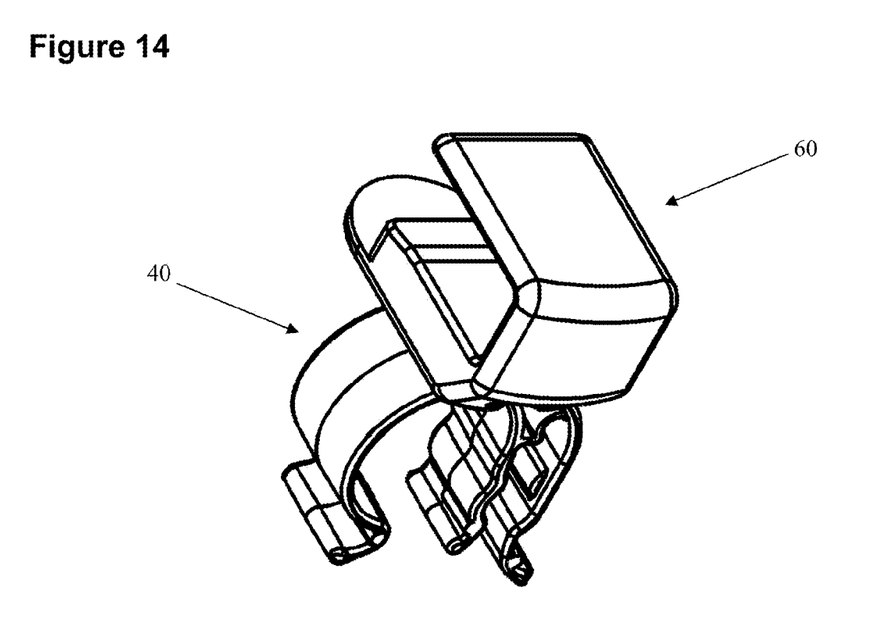
FIG. 14 is a perspective view of the tube holder of FIG. 7 engaged with the clip of FIG. 5.

FIG. 14 shows a tube holder 40 engaged with a clip 60.

Finally, FIGS. 11 and 12 depict a tube cap 70 that may also be used with a clip according to the invention. The tube cap 70 is generally cylindrical, with one closed end 71 and being open at the other end 72. The open end 72 of the cap 70 has a peripheral flange 73, and carries a projecting lug 74 with an enlarged head 75 (similar to the lug 44, 55 and enlarged head 45, 56 of the tube holders described above).

The tube cap 70 is used particularly where medical tubes are disconnected from a patient but are to be reused, or where a breathing system is set up and rested on the machine prior to use. The end of the tube is inserted into the open end of the cap 70, which prevents ingress of dust or the like during the period in which the tube 70 is not in use. The cap 70 may then be coupled to a clip of one of the types described above, such that the tube is stowed in an orderly fashion. It is envisaged that the clip that is used in this way will most commonly be the clip 60 of FIGS. 5 and 6.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A clip for use in a medical tubing management system that is adapted to be engaged with a substrate, the clip comprising:
   a recess or opening adapted to releasably receive a projection of a tube holder, said projection of the tube holder having an enlarged head; and a latch at the recess or opening for retaining the projection releasably received therein; and
   a pair of jaw members arranged to be spaced in a first direction so as to grip the substrate located, in use, between the pair of jaw members, wherein the latch is reversibly actuable in a first plane, which is substantially transverse to the first direction, between a first condition in which the latch retains the projection within the recess or opening and a second condition in which the projection is releasable from the recess or opening, wherein the pair of jaw members are biased by a spring in said first direction to an operative condition in which the jaw members grip the substrate located, in use, between the pair of jaw members, and wherein at least one of said jaw members includes the recess and the latch, and wherein the spring and the latch are integrally formed such that the latch may be resiliently deformed in said first plane and the spring may be resiliently deformed in said first direction.

2. A medical tubing management system, the system comprising:
   (i) a tube holder adapted to receive and retain at least one medical tube, the tube holder comprising a projection having an enlarged head; and
   (ii) a clip adapted to be engaged with a substrate, the clip comprising:
      a recess or opening adapted to releasably receive the projection of the tube holder;
      a latch at the recess or opening for retaining the projection releasably received therein; and
      a pair of jaw members arranged to be spaced in a first direction so as to grip the substrate located, in use, between the pair of jaw members, wherein the latch is reversibly actuable in a first plane, which is substantially transverse to the first direction, between a first condition in which the latch retains the projection within the recess or opening and a second condition in which the projection is releasable from the recess or opening, wherein the pair of jaw members are biased by a spring in said first direction to an operative condition in which the jaw members grip the substrate located, in use, between the pair of jaw members, wherein at least one of said jaw members includes the recess and the latch, and wherein the spring and the latch are integrally formed such that the latch may be resiliently deformed in said first plane and the spring may be resiliently deformed in said first direction.

3. The system as claimed in claim 2, wherein the clip is configured such that it can be engaged with a rail of a type that is commonly present on medical equipment used at a patient's bedside or in an operating theatre.

4. The system as claimed in claim 2, wherein the projection takes the form of a lug or stud.

5. The system as claimed in claim 4, wherein the projection is retained within the corresponding recess or opening by action of gravity.

6. The system as claimed in claim 2, wherein the at least one medical tube is respiratory tubing.

7. The system according to claim 2, wherein the tube holder is adapted to receive and retain at least two medical tubes having different cross-sectional diameters.

8. The system according to claim 2, wherein the tube holder constitutes a holding clip with resilient limbs that define a tube-receiving space.

9. The system according to claim 8, wherein the resilient limbs of the holding clip define a plurality of tube-receiving spaces, so that the holding clip is adapted to couple together a plurality of medical tubes.

10. The system according to claim 9, wherein the resilient limbs are unevenly spaced such that the tube-receiving spaces are of differing dimension.

11. The medical tubing management system of claim 2 wherein the tube holder comprises:
 opposing outer resilient limbs arranged in a generally C-shaped configuration to define a space; and
 one or more intermediate resilient limbs disposed between the outer resilient limbs to divide the space into a plurality of adjacent tube-receiving spaces for releasably receiving the at least one medical tube therein.

12. The system as claimed in claim 11, wherein the tube holder is configured such that the plurality of tube-receiving spaces are of dimensions appropriate to types of differing medical tubes that are commonly used together.

13. The system as claimed in claim 11, wherein at least one of the plurality of adjacent tube-receiving spaces is configured to retain at least two medical tubes between adjacent resilient limbs.

14. The medical tubing management system of claim 11, wherein the one or more intermediate resilient limbs are unevenly spaced such that the tube-receiving spaces are of differing dimension.

* * * * *